(12) United States Patent
Drevik (10) Patent No.: US 7,122,022 B2
(45) Date of Patent: Oct. 17, 2006

(54) ABSORBENT PRODUCT WITH FASTENING ARRANGEMENTS

(75) Inventor: Solgun Drevik, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 413 days.

(21) Appl. No.: 10/169,156

(22) PCT Filed: Dec. 27, 2000

(86) PCT No.: PCT/SE00/02678

§ 371 (c)(1),
(2), (4) Date: Jun. 28, 2002

(87) PCT Pub. No.: WO01/49232

PCT Pub. Date: Jul. 12, 2001

(65) Prior Publication Data

US 2003/0078554 A1    Apr. 24, 2003

(30) Foreign Application Priority Data

Dec. 29, 1999    (SE) ................... 9904839

(51) Int. Cl.
*A61F 13/15* (2006.01)
*A61F 13/20* (2006.01)

(52) U.S. Cl. ............... 604/385.03; 604/389

(58) Field of Classification Search .......... 604/385.01, 604/385.03, 385.101, 385.16, 385.17, 386–387, 604/389

See application file for complete search history.

(56) References Cited

U.S. PATENT DOCUMENTS

| | | | |
|---|---|---|---|
| 3,906,952 A | 9/1975 | Zamist | |
| 4,072,151 A | 2/1978 | Levine | |
| 4,484,919 A | 11/1984 | Sohn et al. | |
| 4,753,648 A * | 6/1988 | Jackson | 604/389 |
| 5,713,886 A * | 2/1998 | Sturino | 604/390 |
| 6,632,210 B1 * | 10/2003 | Glasgow et al. | 604/385.17 |

FOREIGN PATENT DOCUMENTS

| | | |
|---|---|---|
| WO | 96/33683 | 10/1996 |
| WO | 97/39713 | 10/1997 |

* cited by examiner

*Primary Examiner*—Michele Kidwell
(74) *Attorney, Agent, or Firm*—Buchanan Ingersoll & Rooney, PC (57) ABSTRACT

The invention relates to an absorbent product, such as a sanitary towel, a panty liner or an incontinence pad, comprising a liquid-permeable surface layer (102), a liquid-impermeable surface layer (103), and an absorption body (104) arranged between the two surface layers (102, 103). The product also has a front portion (109) and a rear portion (110), and fastening arrangements (113a, 113b, 113c) comprising an adhesive attachment-means zone (120a, 120b, 120c) to be attached to the body of a wearer.

The invention is characterized in that the product is essentially triangular in shape and in that two fastening arrangements (113a, 113b) are arranged on the front portion (109) of the product and one fastening arrangement (113c) is arranged on the rear portion (110) of the product, said fastening arrangements (113a, 113b, 113c) each comprising a part which extends in the form of a strip beyond the periphery of the product and bears the adhesive attachment-means zone (120a, 120b, 120c).

20 Claims, 6 Drawing Sheets

ABSORBENT PRODUCT WITH FASTENING ARRANGEMENTS

BACKGROUND

1. Field of the Invention

The invention relates to an absorbent product, such as a sanitary towel, a panty liner or an incontinence pad, having a longitudinal direction and a transverse direction and comprising a liquid-permeable surface layer, a liquid-impermeable surface layer, and an absorption body arranged between the two surface layers, the liquid-permeable surface layer being intended to face the body of a wearer during use, and the product also having two side edges in its longitudinal direction, a front edge, a rear edge, a front portion and a rear portion, the product also comprising fastening arrangements comprising an adhesive attachment-means zone to be attached to the body of a wearer.

2. Background Art

The production of absorbent products such as incontinence pads, sanitary towels, panty liners or the like has been known for a long time. Such absorbent products are placed in the crotch region of a wearer and absorb discharged bodily fluid. Sanitary towels, panty liners and incontinence pads for slightly incontinent people are usually relatively small and can be accommodated in a pair of ordinary briefs. In order for the absorbent product to stay safely in position during use, it is usual to provide the product with some type of fastening arrangement for fastening the product in the briefs. In this connection, the most common type of fastening arrangement is adhesive which is used to attach the product in the briefs.

However, one problem with absorbent products provided with fastening arrangements which are attached in the underwear, is that the absorbent product tends to move together with the briefs during use. This means that the product may move laterally or that gaps arise between the product and the body of the wearer. The inadequate contact between the body of the wearer and the product can lead to liquid leaking out at the side of the product, or to liquid running on the surface of the product out over the edges of the product. Moreover, an absorbent product which moves in relation to the body of the wearer during use can give rise to an uncomfortable and unreliable feeling.

To solve these problems, it has been proposed that the absorbent product be provided with glued surfaces which are attached to the body. In comparison with products which are attached in the briefs, such an absorbent product has a number of advantages. For example, the absorbent product is located in the same position in relation to the body throughout the entire period of use. As a result, it is possible to obtain a controlled and well-defined target area for the bodily fluid discharged. This means that the absorbent product can be given a design in which the absorbent material is used optimally. By virtue of the fact that the product stays still during use and is not loose, and does not otherwise move in relation to the body of the wearer, a product attached to the body is more leakproof than a product which is attached in the briefs. Furthermore, the product can be worn virtually imperceptibly under normal briefs and, if so desired, the product can be worn without briefs.

U.S. Pat. No. 3,906,952 describes a sanitary towel with narrowing end portions which are adjustably connected to two identical self-adhesive pieces intended to be attached to the body of a wearer. The sanitary towel is applied to the wearer by the self-adhesive pieces being attached to the body just above the genital region and, respectively, above the cleft between the buttocks.

A problem with a product according to U.S. Pat. No. 3,906,952 is that it can feel unstable to wear as a result of the way the self-adhesive pieces are arranged on the sanitary towel. By virtue of the fact that the product is attached to the body at only two attachment points, there is a risk that the product will be unstable or will be turned over to the side as a result of the bodily movements of the wearer. Moreover, there is a risk that the self-adhesive pieces may come away from the body as they are arranged in such a manner on the sanitary towel that they are subjected to point loading during use of the sanitary towel. Another problem associated with absorbent products provided with fastening arrangements which are attached to the body is that they can cause discomfort for the wearer as there is a risk that a fastening arrangement may get caught in the genital hair and that the fastening arrangements may chafe against the skin.

An absorbent product attached to the body is therefore desirable, in which the fastening arrangements are designed and arranged on the product in such a manner that the problems referred to above are minimized or eliminated.

Another problem with absorbent products provided with fastening arrangements which are attached to the body is that the side edges of the product may be folded in over the liquid-receiving region during use. The result of this is that the liquid-impermeable surface layer is exposed to the wearer, which leads to the absorption capacity of the product being reduced. Moreover, folded-in side edges lead to an increased risk of edge leakage. Furthermore, there is a risk that the product is subjected to forces by the muscles in the groin area and the thighs, so that it is pressed together. The result of this is that the risk of edge leakage increases and the product may feel uncomfortable to wear.

An absorbent product attached to the body is therefore desirable, which is designed in such a manner that it is not deformed during use, such as being pressed together or its side edges being folded in over the liquid-receiving region.

SUMMARY

By means of embodiments of the present invention, an absorbent product has been produced, which is intended to be attached to the body of a wearer and essentially eliminates the problems referred to above.

A product of the type indicated in the introduction made according to embodiments of the invention is characterized mainly in that the product is essentially triangular in shape and in that two fastening arrangements are arranged on the front portion of the product and one fastening arrangement is arranged on the rear portion of the product, said fastening arrangements each comprising a part which extends in the form of a strip beyond the periphery of the product and bears the adhesive attachment-means zone.

The fastening arrangements on the front portion are suitably arranged in the regions where the side edges of the product merge with the front edge of the product.

According to one embodiment of the invention, the fastening arrangements are arranged so that they can be seen as a continuation of the side edges of the product and they advantageously have a curved shape. In such an embodiment, the fastening arrangements on the front portion of the product extend away from the remainder of the product both in the longitudinal direction of the product and in its transverse direction.

The front fastening arrangements are attached to the groins of the wearer. The fastening arrangement arranged on the rear portion is attached to the body of a wearer directly above the buttock cleft.

The advantage of arranging two fastening arrangements on the front portion of the product and one fastening arrangement on the rear portion of the product according to an embodiment of the present invention is that the product is stabilized in relation to the wearer by virtue of the fact that the product is held extended and stretched. The risk of the product being unstable or being turned over to the side which is the risk when only two fastening arrangements are arranged on the short sides of the product in line with the longitudinal centre line of the product, is thus reduced.

Moreover, by arranging the fastening arrangements in accordance with an embodiment of the present invention, the force which is developed in a body in motion will not result in the fastening arrangements being subjected to point loading, which means that the risk of the product being over-stressed or even coming away from the wearer is on the whole eliminated.

Another advantage of embodiments of the present invention is that the risk that the fastening arrangements arranged on the front portion of the product will get caught in the genital hair is small as these have a curved shape extending away from the centre line of the product, which means that the fastening arrangements are attached to the groins of the wearer, which are in most cases hairless.

An absorbent product according to embodiments of the present invention suitably has side edges which are curved in the direction in towards the centre line extending in the longitudinal direction of the product. Furthermore, the product according to an embodiment of the present invention can have a width ratio in the transverse direction between the front portion of the product and the rear portion of the product which is 2:1 to 4:1, with the rear portion of the product having a width which does not exceed 40 mm.

A further advantage of a product according to an embodiment of the present invention is that it can be said to have characteristics similar to those of a thong, that is to say that the product fits snugly against the body and stays still. This advantage is achieved with embodiments of the present invention because the shape of the product and the fastening arrangements arranged on the product follow essentially the same contours as a thong. The product is thus leakproof, which is a great advantage if the product is a towel for night use. Moreover, a product according to embodiments of the present invention is completely inconspicuous and can be worn imperceptibly even under very tight-fitting clothing.

A product according to an embodiment of the present invention is designed in such a manner that it is not pressed together between the thighs of the wearer during use. As a result, the risk of leakage out past the side edges is reduced. According to an embodiment of the present invention, moreover, the available absorption area of the product is not affected as there is little risk of the product being pressed together or that the side edges of the product will be folded in over the absorption area as a result of being pressed together by the thighs of the wearer or as a result of bodily movements of the wearer.

According to one embodiment of the invention, the fastening arrangements are fully or partly elastic. This, together with the fact that the fastening arrangements arranged on the product can be arranged separately on the product or constitute projecting portions of one or both surface layers, means that it is possible to custom-make the product for different use situations.

The surface layers of the product do not of course have to be separate material layers, but these layers can be integral with the absorption body. For example, the absorption body can include a foamed material having a liquid-impermeable skin on one of its surfaces. Correspondingly, the liquid-permeable surface layer can consist of an integrated surface on the absorption body.

BRIEF DESCRIPTION OF DRAWINGS

Embodiments of the invention will be described in greater detail below with reference to the exemplary embodiments shown in the appended drawings, in which.

DETAILED DESCRIPTION OF PREFERRED EMBODIMENTS

Figures 1, 2:
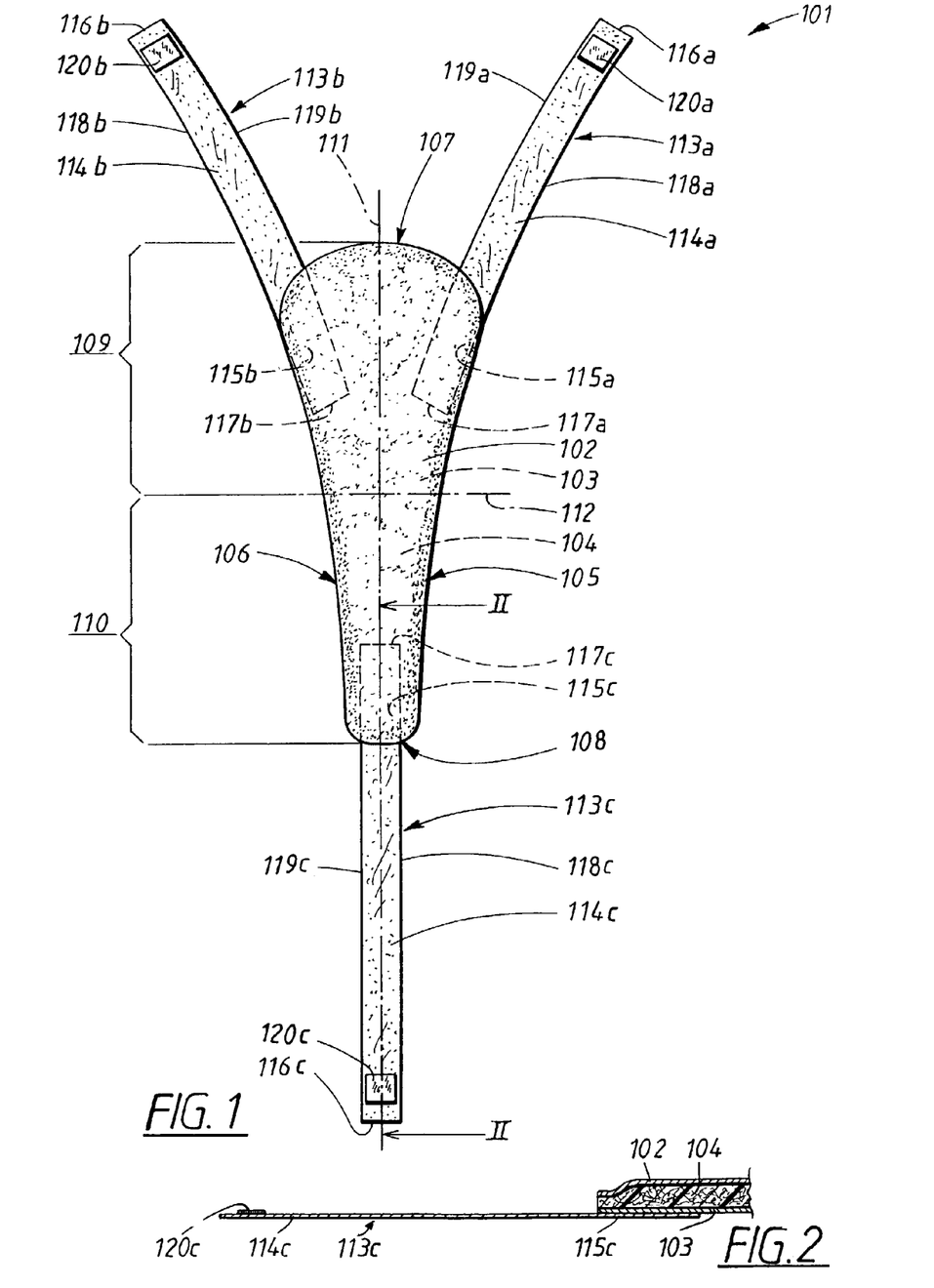
FIG. 1 shows a plan view of a sanitary towel according to an embodiment of the invention, seen from the side which is intended to face the wearer during use of the sanitary towel.
FIG. 2 shows a section along the line II—II through the sanitary towel and a fastening arrangement in FIG. 1.

FIGS. 1 and 2 show a sanitary towel 101 which is essentially triangular in shape with a longitudinal direction and a transverse direction. The sanitary towel 101 comprises a liquid-permeable surface layer 102 arranged on that side of the sanitary towel 101 which is intended to face a wearer during use, a liquid-impermeable surface layer 103 arranged on that side of the sanitary towel 101 which is intended to face away from the wearer during use, and an absorption body 104 enclosed between the two surface layers 102, 103. The sanitary towel 101 can be plane or profiled and may also comprise shaping means (not shown in FIGS. 1 and 2). The sanitary towel 101 also has two side edges 105, 106, two short sides which constitute the front edge 107 and, respectively, the rear edge 108 of the sanitary towel 101, a front portion 109 and a rear portion 110, the rear portion 110 being considerably narrower than the front portion 109. The sanitary towel 101 also has a centre line 111 extending in the longitudinal direction. A longitudinal centre line 111 means a line which extends in the longitudinal direction of the sanitary towel 101 and is arranged equidistantly from the side edges 105, 106 of the sanitary towel 101. The side edges 105, 106, which extend essentially in the longitudinal direction of the sanitary towel 101, have a curvature arranged in such a manner that the side edges curve in towards the longitudinal centre line 111 of the sanitary towel. In the rear portion 110, the side edges 105, 106 run together in the rounded rear edge 108. In the front portion 109, the side edges 105, 106 run together in the essentially curved front edge 107. The sanitary towel also has a centre line 112 extending in the transverse direction. A transverse centre line 112 means a line which extends in the transverse direction of the sanitary towel 101 and is arranged equidistantly from the edges 107, 108 of the sanitary towel 101.

In order that the sanitary towel 101 will not extend so far backwards during use that it shows clearly when it is worn together with a thong or under tight-fitting clothing, the rear portion 110 of the sanitary towel 101 should suitably have a length of between 30 mm and 90 mm. The front portion 109 should suitably have a length of from 60–170 mm. The overall length of the product is suitably 140–260 mm and preferably not greater than 200 mm so as also to fit in thongs with perforated front pieces. The transition between the rear portion 110 and the front portion 109 does of course not take place at a distinct boundary. Furthermore, the rear portion 110 and the front portion 109 do not necessarily divide the sanitary towel 101 into two parts of equal length.

The sanitary towel 101 also comprises three fastening arrangements 113a, 113b, 113c intended to be attached to the body of the wearer. The fastening arrangements 113a, 113b, 113c consist of three strips of material and each have a front strip-shaped part 114a, 114b, 114c and a rear part 115a, 115b, 115c. In this connection, the front part 114a, 114b, 114c means that part of the fastening arrangement 113a, 113b, 113c which extends from the periphery of the sanitary towel 101 and away from the remainder of the sanitary towel 101. Consequently, the rear part 115a, 115b, 115c means that part of the fastening arrangement 113a, 113b, 113c which is arranged on the sanitary towel 101. Moreover, the fastening arrangement 113a, 113b, 113c has two short sides 116a, 116b, 116c; 117a, 117b, 117c and two long sides 118a, 118b, 118c; 119a, 119b, 119c. The fastening arrangement 113a, 113b, 113c comprises an attachment-means zone 120a, 120b, 120c which is arranged on that side of the fastening arrangement 113a, 113b, 113c which will face the body of the wearer during use. The attachment means can consist of pressure-sensitive glue or other means known to the person skilled in the art. The attachment-means zone 120a, 120b, 120c is arranged on the front part 114a, 114b, 114c at a distance from the sides 116a, 116b, 116c; 118a, 118b, 118c; 119a, 119b, 119c of the fastening arrangement 113a, 113b, 113c. Such positioning of the attachment means makes it easier to remove the fastening arrangement 113a, 113b, 113c from the body as it is possible in this way to take hold of a region which is free of attachment means. The size of the attachment-means zone 120a, 120b, 120c should be adapted so that adequately secure fastening is obtained without excessive consumption of attachment means. It is suitable, however, if the width and length of the attachment-means zone 120a, 120b, 120c do not exceed 25 mm.

Two of the fastening arrangements 113a, 113b are arranged on the front portion 109 of the sanitary towel 101, in the region where the side edges 105, 106 merge with the front edge 107. As can be seen from FIG. 1, the fastening arrangements 113a, 113b have an essentially curved shape. It can also be seen from the figure that the fastening arrangements 113a, 113b are arranged in such a manner that they will extend in continuation of the essentially curved side edges 105, 106 and extend essentially away from the remainder of the sanitary towel 101.

The fastening arrangement 113a, 113b should suitably have a maximum width of 30 mm, preferably 10–20 mm, and its front part 114a, 114b should suitably have a length of at least 20 mm.

By virtue of the fact that the fastening arrangements 113a, 113b are curved, the risk is reduced of these being crumpled during fastening to the body in the region of the groins and causing discomfort due to chafing. With such a design, the risk of the fastening arrangements 113a, 113b being crumpled during use is also reduced.

The fastening arrangement 113c arranged on the rear edge 108 of the sanitary towel 101 extends in imaginary continuation of the longitudinal centre line 111 away from the remainder of the sanitary towel 101, see FIG. 1. The fastening arrangement 113c is arranged equidistantly from the side edges 105, 106. As can be seen from FIG. 1, the fastening arrangement 113c is rectangular in shape with a maximum width of 30 mm, preferably 15–25 mm. The front part 114c of the fastening arrangement 113c should suitably have a length of at least 50 mm.

In order to achieve secure and comfortable fastening of the towel 101, it is advantageous if the length I marked in FIG. 1 is 470±50 mm. The length of the front strip-shaped part 115a, 115b, 115c of the fastening arrangements 113a, 113b, 113c should therefore be dimensioned according to the length of the product.

It is possible to design the front part 114c of the fastening arrangement 113c, in a region which includes the short side 116c, so that it ends in the shape of, for example, an inverted equilateral triangle or drop (not shown in the figure). In this connection, the short side 116c of the fastening arrangement 113c will constitute the base of the triangle or the rounded end of the drop. The "pointed" ends of the triangle and the drop are cut off in such a manner that the width of the remaining part of the "point" corresponds to the width of the remaining front part 114c. The fastening arrangements 113a, 113b arranged on the front edge 107 can of course also be designed in a similar manner. Such shapes can be suitable when a larger attachment area is desired on account of the size of the product. It can also be suitable when the sanitary towel is used together with a thong because modern thongs have a fabric portion which narrows from the rear band down towards the buttock cleft and, directly above the buttock cleft, takes the form of a string.

In order to obtain secure fastening to the body with the shapes (not shown) described above, one or more attachment-means zones can be arranged in a suitable manner. However, the attachment-means zones should be arranged at a distance from the periphery of the fastening arrangement in a similar manner to that described in connection with FIG. 1.

It is of course also possible, for purely aesthetic reasons, to design the end of the front part 114a, 114b, 114c as a flower or the like.

The fastening arrangements 113a, 113b, 113c can consist of non-woven material, or a different type of textile material, which may be knitted, woven, braided or crocheted. Plastic material can also be used. For reasons of comfort, however, the latter is less preferable. It is also possible to design the fastening arrangements 113a, 113b, 113c so that they are entirely or partly elastic. In this connection, elastic means such as, for example, threads or bands can be arranged along the entire fastening arrangement 113a, 113b, 113c or on parts thereof. Alternatively, the fastening arrangements 113a, 113b, 113c can consist entirely or partly of elastic material, for example elastic non-woven.

FIG. 2 shows a section through the sanitary towel 101 and the fastening arrangement 113c along the line II—II. As can be seen from FIG. 2, the liquid-permeable surface layer 102 is essentially the same shape as the absorption body 104. The liquid-impermeable surface layer 103 is also shaped like the absorption body 104. The liquid-permeable surface layer 102, the liquid-impermeable surface layer 103 and the absorption body 104 are connected to one another in a conventional manner, for example connected at a join along the edges 105, 106, 107, 108 of the sanitary towel by gluing or by welding using ultrasound.

The liquid-permeable surface layer 102 is of conventional type and can therefore consist of any liquid-permeable material suitable for the purpose. Examples of such material are various types of thin non-woven material, perforated plastic films, net material, liquid-permeable foam material or the like. The liquid-permeable surface layer 102 can be made from two or more different materials which can be arranged in different regions in order to provide different functions of the surface layer.

The liquid-blocking surface layer 103 suitably consists of, for example, plastic film, hydrophobic non-woven or non-woven coated with resin or another liquid-impermeable material, or another material suitable for the purpose.

The absorption body 104 can be what is known as an airlaid cellulose body or be made from any suitable absorbent material. Superabsorbents are such a suitable absorption material because the available absorption space is small and superabsorbents have great absorption capacity per unit of weight or volume.

Other suitable absorbent materials for use in the absorption body 104 are, for example, cellulose fluff pulp, absorbent bound fiber layers, tissue layers, absorbent foam, peat or the like. The absorption body can also contain superabsorbent polymers, that is to say polymers with the capacity to absorb several times their own weight of liquid while forming a liquid-containing gel. Superabsorbents are usually in the form of particles, flakes, fibers, granules or the like. The superabsorbent material can be used on its own or together with another absorbent material.

It can also be seen from FIG. 2 that the fastening arrangement 113c is arranged on the liquid-impermeable surface layer 103 on the side which will face away from the wearer during use. FIG. 2 also shows that the rear part 115c of the fastening arrangement 113c extends along the centre line 111 in towards the transverse centre line 112 of the sanitary towel 101. The rear part 115c is suitably arranged on the sanitary towel 101 so that secure fixing is obtained. The fastening arrangement 113c and the liquid-impermeable surface layer 103 are suitably connected to one another in a conventional manner, for example by gluing, sewing, or by welding using heat or ultrasound. The fastening arrangements 113a, 113b are fixed to the liquid-impermeable surface layer 103 in a corresponding manner.

It is also possible to fix the fastening arrangements 113a, 113b, 113c on that side of the liquid-impermeable surface layer 103 which faces the wearer during use. Instead, it is of course possible to fix the fastening arrangements 113a, 113b, 113c to the liquid-permeable surface layer 102. This is to be seen as less advantageous, however, because such fastening would have a negative effect on the liquid-admission capacity of the sanitary towel 101. Moreover, if the fastening arrangements 113a, 113b, 113c are fixed on that side of the liquid-permeable surface layer 102 which faces the wearer during use, there is a risk that the sanitary towel 101 may chafe against the skin of the wearer, which would result in the sanitary towel 101 not feeling comfortable to wear. A solution to the problems which arise in the event of the fastening arrangements 113a, 113b, 113c being fixed to the liquid-permeable surface layer 102 is for the rear part 115a, 115b, 115c to be designed in such a manner that it does not extend further into the sanitary towel than the width of the join which connects the surface layers 102, 103 and the absorption body 104 together. In the event of narrow joins, however, this cannot be considered an advantageous embodiment either, because secure fixing of the fastening arrangements 113a, 113b, 113c cannot always be guaranteed.

Figure 3:
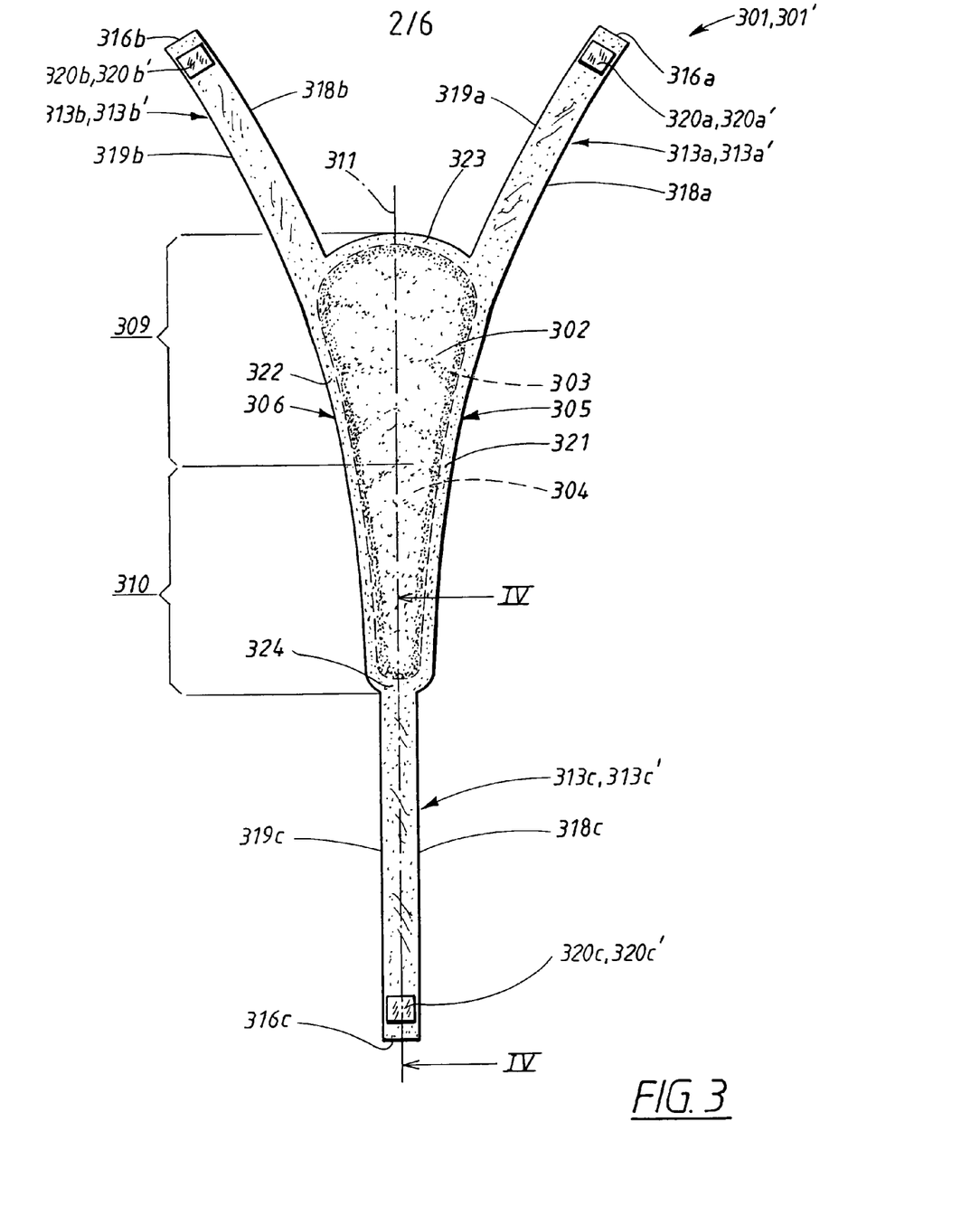
FIG. 3 shows a plan view of a sanitary towel according to an embodiment of the invention seen from the side which is intended to face the wearer during use of the sanitary towel.

FIG. 3 shows a sanitary towel 301 according to an embodiment of the invention. The figure shows diagrammatically a plan view of the sanitary towel 301, seen from the side which is intended to face the wearer during use of the sanitary towel 301. In a similar manner to the sanitary towel 101 described in FIGS. 1 and 2, the sanitary towel 301 comprises an absorption body 304 enclosed between a liquid-permeable surface layer 302 and a liquid-impermeable surface layer 303. The surface layers 302, 303 are essentially the same shape as but have a slightly greater planar extent than the absorption body 304. The surface layers 302, 303 therefore extend a little way beyond the edges of the absorption body 304 where they are joined together with one another in a conventional manner, for example by gluing, sewing or welding using heat or ultrasound, and form covering edges 321, 322, 323, 324.

Figure 4A:
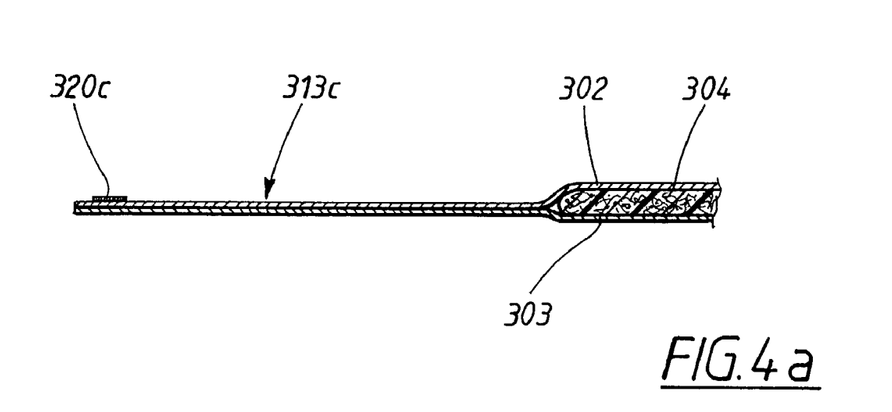
FIG. 4*a* shows a section along the line IV—IV through the sanitary towel and a fastening arrangement in FIG. 3.

An alternative embodiment of the invention is shown in FIG. 4a which shows a section through the sanitary towel 301 and a fastening arrangement 313c along the line IV—IV. The fastening arrangement 313c, arranged on the rear portion 310 of the sanitary towel, constitutes a projecting portion of the covering edge 324, the portion being arranged in imaginary continuation of the longitudinal centre line 311 and equidistantly from the side edges 305, 306. In this connection, the covering edge 324 merges continuously with the sides 316c, 318c, 319c of the fastening arrangement 313c (see FIG. 3). In a similar manner to the fastening arrangement 113c described in connection with FIGS. 1 and 2, the fastening arrangement 313c comprises an attachment-means zone 320c which is arranged in a manner corresponding to that described in connection with FIGS. 1 and 2.

It can also be seen from FIG. 3 that two fastening arrangements 313a, 313b are arranged on the front portion 309 of the towel 301. In this connection, the fastening arrangements 313a, 313b constitute projecting portions of the longitudinal covering edges 321, 322 in the region between said covering edges 321, 322 and the covering edge 323. In this connection, the covering edges 321, 322, 323 merge continuously with the sides 316a, 318a, 319a; 316b, 318b, 319b of the fastening arrangements 313a, 313b. As can be seen from FIG. 3, the fastening arrangements 313a, 313b will extend in continuation of the essentially curved sides edges 305, 306 and extend essentially away from the remainder of the sanitary towel 301. An attachment-means zone 320a, 320b is arranged on the fastening arrangement 313a, 313b in a manner corresponding to that described in connection with FIGS. 1 and 2.

Figure 4B:
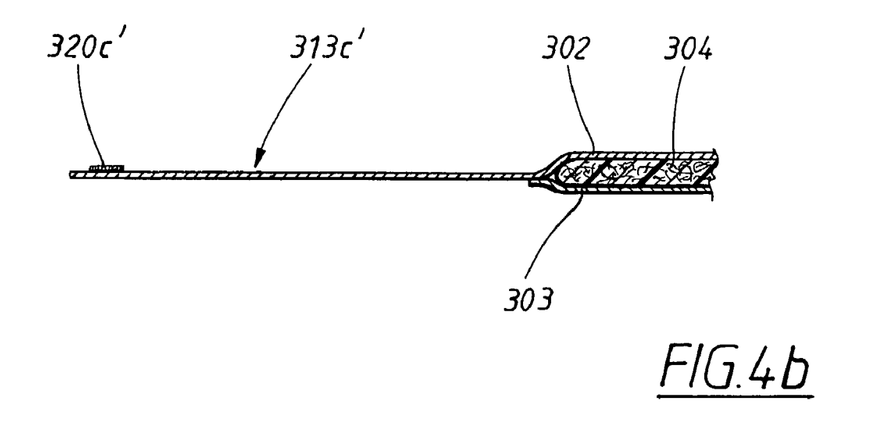
FIG. 4*b* shows a section along the line IV—IV through the sanitary towel and a fastening arrangement, showing an alternative embodiment of the sanitary towel in FIG. 3.

A further alternative embodiment of the invention is shown in FIG. 4b which shows a section through a sanitary towel 301' and a fastening arrangement 313c' along the line IV'—IV'. What distinguishes the sanitary towel 301' from that described in FIG. 4a is that the fastening arrangement 313c' constitutes a projecting portion of only the liquid-permeable surface layer 302. In a corresponding manner, the fastening arrangements 313a', 313b' constitute projecting portions of only the liquid-permeable surface layer 302. The attachment-means zones 320a', 320b', 320c' are arranged on the fastening arrangements 313a', 313b', 313c' in a manner corresponding to that described in connection with FIG. 4a.

The embodiment shown in FIG. 4b is more advantageous than that shown in FIG. 4a. This is because the fastening arrangement 313c' in FIG. 4b does not have a liquid-impermeable surface layer on the side which faces away from the wearer during use. The risk of moisture forming on the skin of the wearer in the region where the fastening arrangement 313c' is applied, and thus the risk of the fastening arrangement 313c' chafing against the skin, is reduced. It follows from this that an embodiment in which the fastening arrangements constitute projecting portions of the liquid-impermeable surface layer (not shown in the figure) is a possible but less preferable embodiment.

If the fastening arrangements constitute projecting portions of a surface layer consisting of non-woven material, the fastening arrangements can have a certain elasticity. This can be brought about by orienting the fibers in the surface layer in the same direction, preferably in the transverse direction of the product.

The embodiments described in FIGS. 3, 4a and 4b are advantageous from the point of view of process engineering because the fastening arrangements are cut out of the same piece of material as the surface layers. On the other hand, the embodiment described in connection with FIGS. 1 and 2 affords greater freedom of choice in terms of selecting the material for the various fastening arrangements because they are fixed separately to one of the surface layers.

Figure 5:
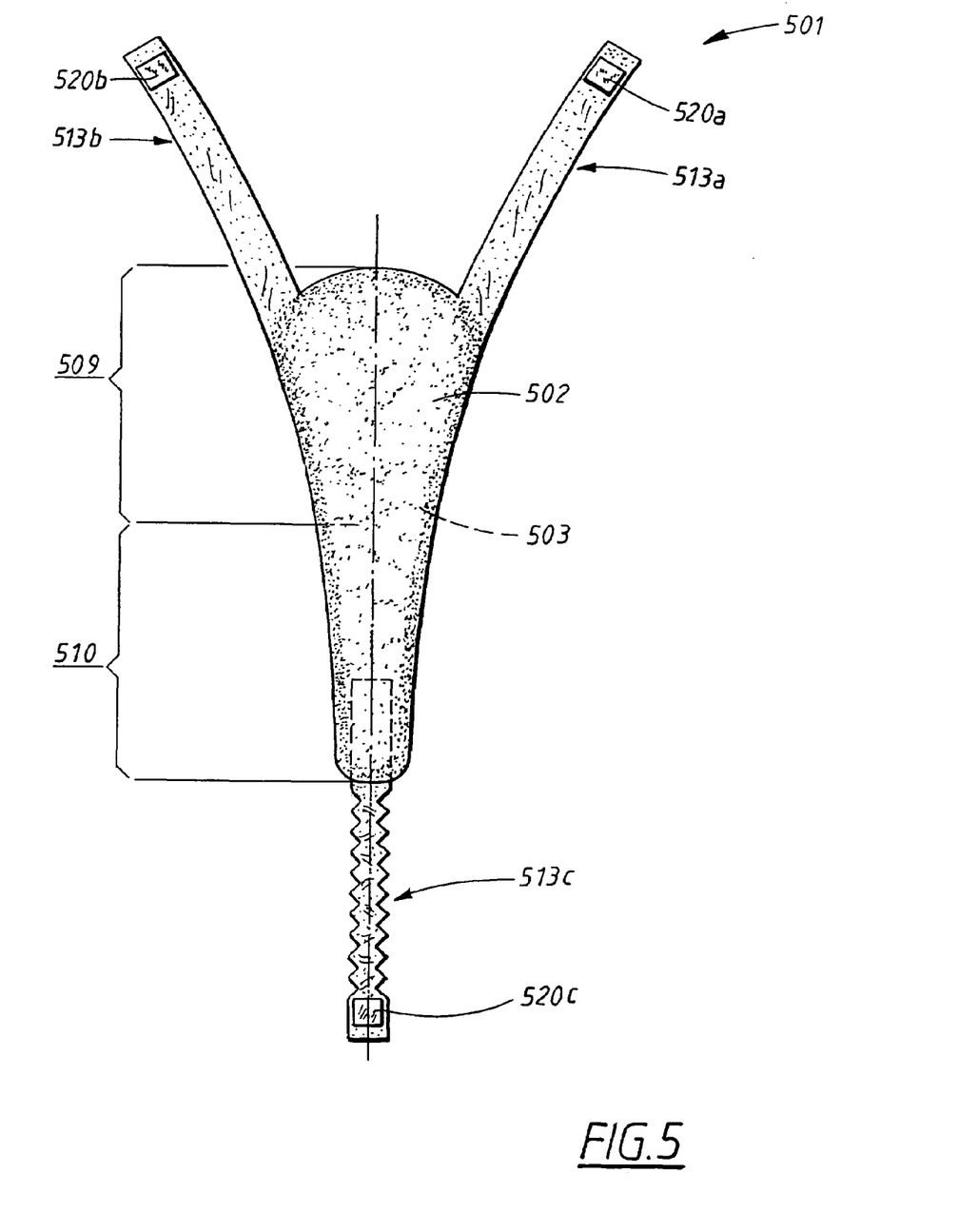
FIG. 5 shows a plan view of a sanitary towel according to an embodiment of the invention seen from the side which is intended to face the wearer during use of the sanitary towel.

Another possible embodiment of the invention is shown in FIG. 5. FIG. 5 shows diagrammatically a plan view of a sanitary towel 501, seen from the side which is intended to face the wearer during use of the sanitary towel 501. The sanitary towel 501 can, for example, be of the type shown in FIG. 1. What distinguishes the sanitary towel 501 from that shown in FIG. 1 is that the fastening arrangements 513a, 513b arranged on the front portion 509 constitute projecting portions of at least one surface layer 502, 503 in a similar manner to that described in connection with FIGS. 3, 4a and 4b. Moreover, the fastening arrangement 513c arranged on the rear portion 510, which is fixed in a manner corresponding to that described in connection with FIG. 1, is provided with elastic means. By providing the fastening arrangement 513c with elastic means, a more flexible adaptation to the movements of the body is obtained. The elastic means can consist of threads or bands. Alternatively, elastic non-woven can be used. The elastic means can of course be arranged so that the fastening arrangement 513c is only partly elastic (not shown in the figure). The attachment-means zones 520a, 520b, 520c are arranged on the fastening arrangements 513a, 513b, 513c in a manner corresponding to that described in connection with FIG. 4a.

Figure 6:
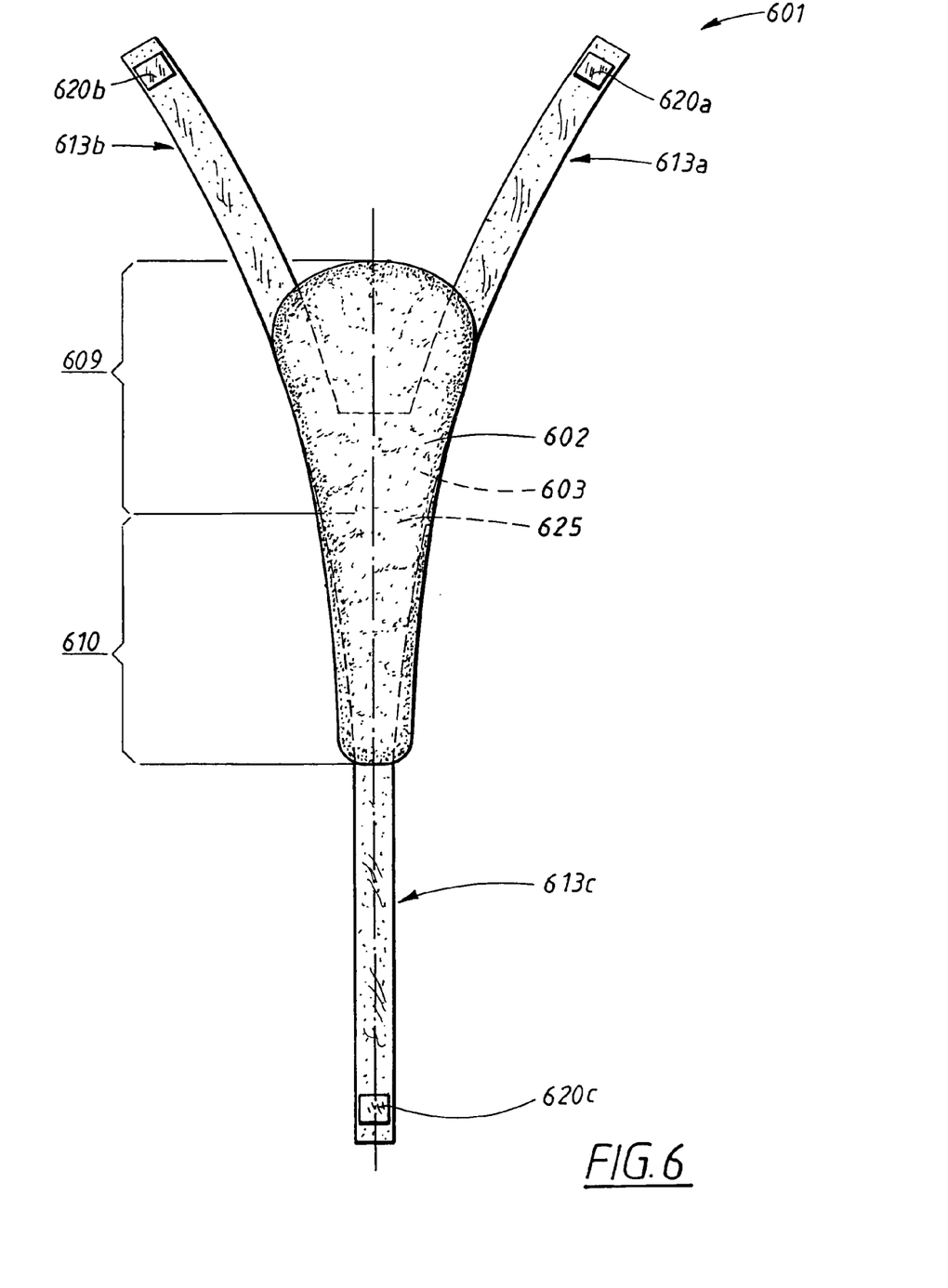
FIG. 6 shows a plan view of a sanitary towel according to an embodiment of the invention seen from the side which is intended to face the wearer during use of the sanitary towel.

FIG. 6 shows another possible embodiment of the invention. The figure shows diagrammatically a plan view of a sanitary towel 601, for example of the type shown in FIG. 1, seen from the side which is intended to face the wearer during use of the sanitary towel 601. What distinguishes the sanitary towel 601 from that shown in FIG. 1 is that the fastening arrangements 613a, 613b, 613c constitute projecting portions of a separate piece 625 intended to be fixed to the sanitary towel 601. The piece 625 is essentially shaped like the letter Y, the fastening arrangements 613a, 613b arranged on the front portion 609 constituting the upper arms of the Y and the fastening arrangement 613c arranged on the rear portion 610 constituting the leg of the Y. The piece 625 is preferably fixed to the liquid-impermeable surface layer 603. FIG. 6 shows a case in which the piece 625 is fixed to that side of the liquid-impermeable surface layer 603 which faces away from the wearer during use. The piece 625 and the liquid-blocking surface layer 603 are connected to one another in a conventional manner, for example by gluing, sewing or by welding using heat or ultrasound. It is of course also possible to fix the piece 625 to the liquid-permeable surface layer 602 but this is to be seen as less advantageous as it would have a negative effect on the liquid-admission capacity of the sanitary towel 601.

The attachment-means zones 620a, 620b, 620c are arranged on the fastening arrangements 613a, 613b, 613c in a manner corresponding to that described in connection with FIG. 1.

Figure 7:
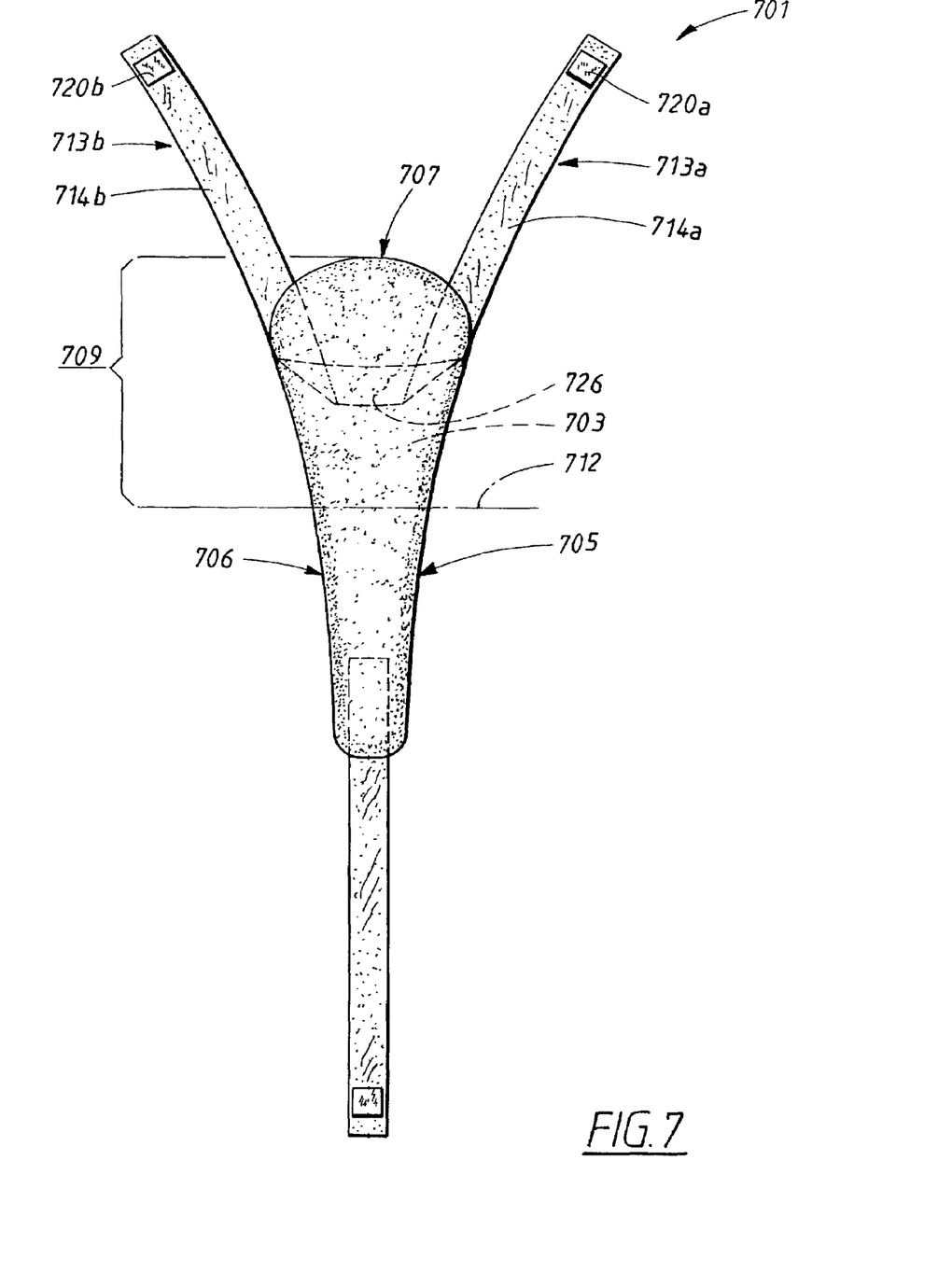
FIG. 7 shows a plan view of a sanitary towel according to an embodiment of the invention seen from the side which is intended to face the wearer during use of the sanitary towel.

FIG. 7 shows diagrammatically a plan view of a sanitary towel 701 seen from the side which is intended to face the wearer during use. The sanitary towel 701 shown in FIG. 7 can, for example, be of the type shown in FIG. 1. What distinguishes the sanitary towel 701 from that shown in FIG. 1 is that the fastening arrangements 713a, 713b arranged on the front portion 709 constitute projecting portions of a strip-shaped piece 726 which is arranged on the front portion 709 of the sanitary towel 701 parallel to the transverse centre line 712. The strip-shaped piece 726 can have straight or curved long sides. The strip-shaped piece 726 is arranged on the liquid-impermeable surface layer 703. In this connection, the strip-shaped piece 726 is arranged so that the fastening arrangements 713a, 713b will essentially extend in continuation of the longitudinal side edges 705, 706 away from the remainder of the sanitary towel 701. This is brought about by virtue of the fact that, on fastening to the surface layer 703, the strip-shaped piece 726 is folded in the region inside the side edges 705, 706 so that the front part 714a, 714b is folded up towards the front edge 707. Compared with the embodiment described in FIGS. 1 and 2, the embodiment in FIG. 7 results in simplified production of the sanitary towel 701 and also reduces material waste in the case of transverse production of the sanitary towel 701. It is of course also possible to fix the strip-shaped piece 726 to the liquid-permeable surface layer 702 but this is to be seen as less advantageous because it would have a negative effect on the liquid-admission capacity of the sanitary towel 701.

The fastening arrangement 713c arranged on the rear portion 710 is fixed in a manner corresponding to that described in connection with FIG. 1. The attachment-means zones 720a, 720b, 720c are arranged on the fastening arrangements 713a, 713b, 713c in a manner corresponding to that described in connection with FIG. 1.

Before use of the sanitary towels shown in the figures, the attachment-means zones are suitably protected in a conventional manner, for example by being covered by a protective layer of paper or plastic which has been treated with silicone or embossed so as to be removable when the sanitary towels are to be used. The attachment-means zones can of course be covered with any other suitable protection which is easy to remove.

The invention is not to be considered as being limited to the embodiments above. These are intended only to describe embodiments of the invention.

It is possible to combine characteristics from different embodiments, in particular different ways of arranging the fastening arrangement on the product, with one another within the scope of the invention. See, for example, FIGS. 1, 3, 6 and 7. Furthermore, the end of the front strip-shaped part of the fastening arrangement, in the region of the short side, can of course be designed individually for each of the fastening arrangements. Compare the triangle or drop shape described previously. It is of course also possible to design the fastening arrangements individually so that one, two or all three are entirely or partly elastic or not elastic at all. Moreover, the sanitary towels in FIGS. 1 and 3 have a different design in order to illustrate the possibility for variation within the scope of the invention. Within the scope of the invention, other shapes of the sanitary towel are of course also possible provided the sanitary towel has a very narrow rear portion and a relatively wide front portion.

Although the invention has been described in connection with a sanitary towel, it is of course also possible to apply the invention to a panty liner or an incontinence pad.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. An absorbent product having a longitudinal direction and a transverse direction and comprising
   a liquid-permeable surface layer,
   a liquid-impermeable surface layer,
   an absorption body arranged between the surface layers, the liquid-permeable surface layer being intended to face the body of a wearer during use,
   two side edges in the longitudinal direction,
   a front edge,
   a rear edge,
   a front portion and a rear portion, and
   fastening arrangements comprising an adhesive attachment zone to be attached to the body of a wearer,
   the absorption body in its planar extension being essentially triangular in shape with the front portion being wider than the rear portion, and
   two of the fastening arrangements being arranged on the front portion of the product and extending in a diverging manner from the absorption body such that distal portions of the two fastening arrangements, which include the adhesive attachment zones, are farther apart from each other than the proximal portions of the two fastening arrangements and one of the fastening arrangements being arranged on the rear portion of the product,
   said fastening arrangements each comprising a part which extends in a form of a strip from a periphery of the product and bears the adhesive attachment zone.

2. An absorbent product according to claim 1, in which the fastening arrangements on the front portion of the product are arranged in a region where the side edges of the product merge with the front edge of the product.

3. An absorbent product according to claim 1, in which the fastening arrangements on the front portion of the product can be seen as a continuation of the side edges of the product and have a shape which is curved away from a centre line extending in the longitudinal direction of the product.

4. An absorbent product according to claim 1, in which the front strip-shaped part of the fastening arrangements arranged on the front portion of the product has a length of at least 20 mm.

5. An absorbent product according to claim 1, in which the fastening arrangement on the rear portion of the product is arranged on the rear edge of the product extending away from a remainder of the product along an imaginary longitudinal centre line of the product.

6. An absorbent product according to claim 1, in which the fastening arrangement on the rear portion of the product is essentially rectangular in shape.

7. An absorbent product according to claim 1, in which the front strip-shaped part of the fastening arrangement arranged on the rear portion of the product has a length of at least 50 mm.

8. An absorbent product according to claim 1, in which the side edges of the product are curved in a direction in towards a centre line extending in the longitudinal direction of the product.

9. An absorbent product according to claim 1, in which the product has a width ratio in the transverse direction between the front portion of the product and the rear portion of the product which is 2:1–4:1, the rear portion of the product having a width which does not exceed 40 mm.

10. An absorbent product according to claim 1, in which the fastening arrangements are arranged on one of the surface layers.

11. An absorbent product according to claim 1, in which at least one of the fastening arrangements comprises a portion of at least one surface layer.

12. An absorbent product according to claim 1, in which the length of the product does not exceed 260 mm.

13. An absorbent product according to claim 1, in which the fastening arrangements have a width which does not exceed 30 mm.

14. An absorbent product according to claim 1, in which the fastening arrangements on the front portion and the fastening arrangement on the rear portion have a width of 10–20 mm and, respectively, 15–25 mm.

15. An absorbent product according to claim 1, in which the fastening arrangements consist of non-woven material.

16. An absorbent product according to claim 1, in which the fastening arrangements are entirely or partly elastic.

17. An absorbent product according to claim 1, in which the attachment zone is arranged at a distance from sides of the fastening arrangement.

18. An absorbent product according to claim 1, wherein the absorbent product is a sanitary napkin, panty liner, or incontinence pad.

19. An absorbent product according to claim 1, wherein the length of the product does not exceed 200 mm.

20. An absorbent product according to claim 1, wherein the fastening arrangements comprise a non-woven material.

* * * * *